United States Patent
Roe et al.

(10) Patent No.: US 9,050,063 B2
(45) Date of Patent: Jun. 9, 2015

(54) SYSTEMS AND METHODS FOR DETERMINING SUITABILITY OF A MECHANICAL IMPLANT FOR A MEDICAL PROCEDURE

(71) Applicant: Sandance Technology LLC, Princeton, NJ (US)

(72) Inventors: Michael Roe, Princeton, NJ (US); Steven Haas, New York, NY (US)

(73) Assignee: SanDance Technology LLC, Princeton, NJ (US)

( * ) Notice: Subject to any disclaimer, the term of this patent is extended or adjusted under 35 U.S.C. 154(b) by 26 days.

(21) Appl. No.: 13/835,494

(22) Filed: Mar. 15, 2013

(65) Prior Publication Data

US 2013/0269714 A1    Oct. 17, 2013

Related U.S. Application Data

(60) Provisional application No. 61/617,942, filed on Mar. 30, 2012.

(51) Int. Cl.
*G06F 19/00*    (2011.01)
*A61B 19/00*    (2006.01)

(52) U.S. Cl.
CPC .............. *A61B 19/00* (2013.01); *G06F 19/324* (2013.01); *A61B 19/50* (2013.01); *A61B 2019/442* (2013.01); *A61B 2019/508* (2013.01)

(58) Field of Classification Search
USPC ......................................................... 235/375
See application file for complete search history.

(56) References Cited

U.S. PATENT DOCUMENTS

| 8,430,320 | B2 | 4/2013 | Prpa |
| 8,457,757 | B2 | 6/2013 | Cauller et al. |
| 2003/0200120 | A1 | 10/2003 | Binkert |
| 2006/0140139 | A1* | 6/2006 | DiSilvestro et al. ......... 370/310 |
| 2013/0053680 | A1* | 2/2013 | Frey ............................ 600/411 |

FOREIGN PATENT DOCUMENTS

WO    2010068212 A1    6/2010

OTHER PUBLICATIONS

Search Report from PCT Publication No. PCT/US13/33254; filed Mar. 21, 2013; 4 pgs.
Written Opinion from PCT Publication No. PCT/US13/33254; filed Mar. 21, 2013; 5 pgs.

* cited by examiner

*Primary Examiner* — Christle I Marshall
(74) *Attorney, Agent, or Firm* — Chiesa Shahinian & Giantomasi PC

(57) ABSTRACT

Stored information comprising product use information for each of a plurality of mechanical implants is maintained. Data identifying a mechanical implant is received, during a medical procedure. Suitability of the mechanical implant is determined, during the medical procedure, based on the data and the stored information.

20 Claims, 8 Drawing Sheets

| | Implant Identifier 281 | Implant Name 282 | Implant Type 283 | Lot No. 284 | Implant System 285 | Manufacturer 286 | Expiration Date 287 | Recall Information 288 | Rule Set 289 |
|---|---|---|---|---|---|---|---|---|---|
| 291 | ID-1 | Knee A | Type 1 | 1000 | System 2 | Company-1 | 01/15/2023 | Recall issued MM/DD/YYYY | Rule Set 1 Location |
| 292 | ID-2 | Knee B | Type 2 | 52300 | System 2 | Company-1 | 01/15/2023 | Recall issued MM/DD/YYYY | Rule Set 2 Location |
| 293 | ID-3 | Artificial Knee P-1 | Type 1 | 16040 | System 3 | Company-2 | None | None | Rule Set 3 Location |
| 294 | ID-4 | Artificial Knee P-2 | Type 2 | 3300 | System 3 | Company-2 | None | None | Rule Set 4 Location |
| 295 | ID-5 | Knee Insert P-6 | Type 2 | 267 | System 4 | Company-2 | None | None | Rule Set 5 Location |

| | Medical Procedure | Expected Mechanical Implants |
|---|---|---|
| 271 | Procedure A | Type 1, Type 2 |
| 272 | Procedure B | Type 3, Type 4, Type 5 |
143 → ; 261, 262
FIG. 2B
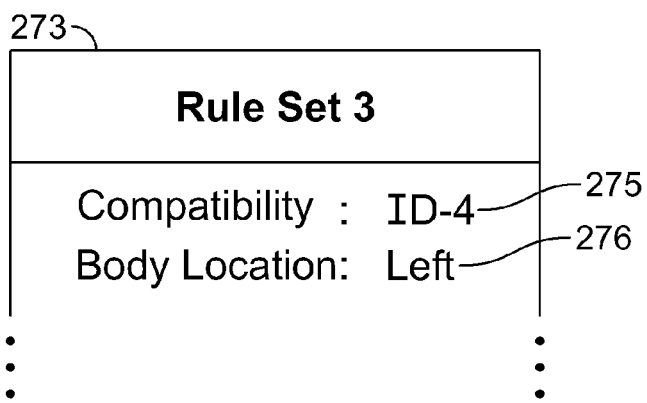
FIG. 2C
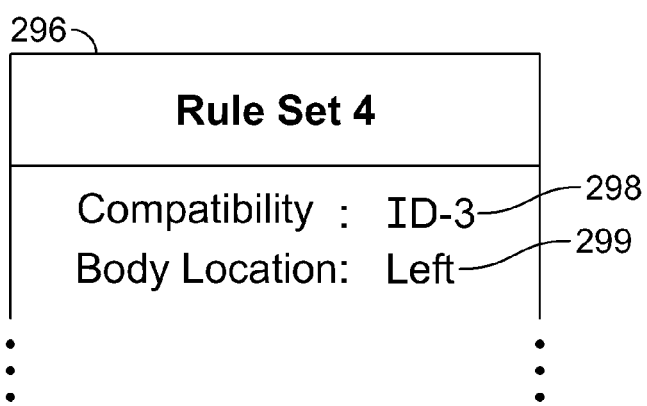
FIG. 2D

SYSTEMS AND METHODS FOR DETERMINING SUITABILITY OF A MECHANICAL IMPLANT FOR A MEDICAL PROCEDURE

This application claims the benefit of U.S. Provisional Patent Application No. 61/617,942, filed on Mar. 30, 2012, which is incorporated herein in its entirety.

TECHNICAL FIELD

This specification relates generally to systems and methods for facilitating use of a mechanical implant in a medical procedure, and more particularly, to systems and methods for determining suitability of a mechanical implant for a medical procedure.

BACKGROUND

An implant is a medical device that is manufactured to replace or augment a biological structure, such as a joint or organ. Implant surgery is a long and complex operation requiring surgeons with many years of training and experience to embed multiple medical devices, known as "implant systems", into the patient. An implant system is a sophisticated series of implant parts that can vary by attributes such as laterality (i.e., which side the implant is designed to support), size, material and construction, and is designed by the manufacturer to work together to replace or augment the biological structure. There are strict rules that govern the parts' compatibility with the patient and with each other, and these rules vary by implant procedure, manufacturer and system, and can be very complex. As the market for medical device implants has grown, so has the number of manufacturers marketing multiple systems, which has led to a proliferation of these compatibility rules.

While it is critical that compatibility rules are followed, they are not always well documented or internalized within the medical community. A 2009 survey by the American Academy of Orthopedic Surgeons (AAOS) found that 53% of the respondents had observed a medical error in the past six months, and of those, 2.6% related to having the wrong implant.

To reduce the possibility of error, it is the practice of most hospitals to have a manufacturer's representative attend all implant surgeries, and/or to have the surgeons call a "time out" to verify selected implants. In addition, efforts have been made to standardize the often confusing manufacturers labels, but with little success thus far. Indeed, there remain multiple points of failure during any procedure, and the consequences of error can be significant.

The exact process by which medical devices are selected, retrieved and verified in the operating room varies by type of procedure. However, most follow the same general flow, and have similar points of failure.

For example, while the manufacturer, system and laterality are typically selected in advance, the surgeon will make the final determination of the specific parts (size, material, construction etc.) after visual inspection of the biological structure. Sometimes, the surgeon may select an incompatible combination of parts. After the specific parts have been selected, the surgeon typically notifies an assistant, such as a nurse or the manufacturer's representative. Sometimes, the surgeon's assistant may misunderstand the surgeon's instructions. While the surgeon waits, the assistant will retrieve the appropriate parts from another location, which are then visually inspected while still in their boxes by the assistant to ensure that they are consistent with the surgeon's instructions. However, box labels are typically small and cryptic, and their design varies by manufacturer. Sometimes, the assistant may properly understand the surgeon's instructions, but then misread the part labels and retrieve the wrong parts.

Typically these steps occur during a critical point in the procedure after which the surgeon has made an incision and is waiting to proceed. Naturally, time is of the essence, which can increase pressure on the assistant and the likelihood of human error. Further, even if the manufacturer's rules have been adhered to, it is possible that any one part might be obsolete, expired or have been recalled.

SUMMARY

In accordance with an embodiment, a method of verifying a suitability of a mechanical implant for a medical procedure is provided. Stored information comprising product use information for each of a plurality of mechanical implants is maintained. First data identifying a mechanical implant is received, during a medical procedure. Suitability of the mechanical implant is determined, during the medical procedure, based on the first data and the stored information.

In one embodiment, a bar code associated with the mechanical implant is detected, and the mechanical implant is identified based on the bar code and the stored information.

In one embodiment, the product use information comprises second information indicating whether the mechanical implant is compatible with a second mechanical implant. Second data identifying the second implant is received during the medical procedure, and a determination is made, during the medical procedure, whether the mechanical implant is compatible with the second mechanical implant, based on the data, the second data, and the second information. For example, the second information may comprise a stored rule.

In another embodiment, the product use information comprises recall information indicating whether a recall of the mechanical implant has been issued. A determination is made, during the medical procedure, that a recall of the mechanical implant has been issued, based on the data and the recall information.

In another embodiment, the product use information comprises expiration information indicating whether an expiration date of the mechanical implant has passed. A determination is made, during the medical procedure, that the expiration date of the mechanical implant has passed, based on the data and the expiration information.

In another embodiment, a stored rule associated with the mechanical implant is accessed, and suitability of the mechanical implant is determined, based on the data, the stored information, and the rule.

In accordance with another embodiment, a system includes a first memory storing information comprising product use information for each of a plurality of mechanical implants, and a scanner. The system also includes a second memory storing computer program instructions, and a processor communicatively coupled to the second memory. The processor is configured to execute the computer program instructions which, when executed on the processor, cause the processor to perform operations including receiving, during a medical procedure, from the scanner, data identifying a mechanical implant, retrieving from the first memory selected information related to the mechanical implant, and determining, during the medical procedure, suitability of the mechanical implant, based on the data and the selected information.

In another embodiment, the product use information specifies a body location associated with the identified mechanical implant. Second data identifying a body location associated with the medical procedure is received, and a determination is made, during the medical procedure, concerning suitability of the mechanical implant, based on the data, the second data, and the stored information.

These and other advantages of the present disclosure will be apparent to those of ordinary skill in the art by reference to the following Detailed Description and the accompanying drawings.

BRIEF DESCRIPTION OF THE DRAWINGS

FIG. 2A shows a mechanical implant database in accordance with an embodiment;

FIG. 2B shows a medical procedure table in accordance with an embodiment;

FIG. 2C shows a rule set in accordance with an embodiment;

FIG. 2D shows a rule set in accordance with an embodiment;

DETAILED DESCRIPTION

Figure 1:
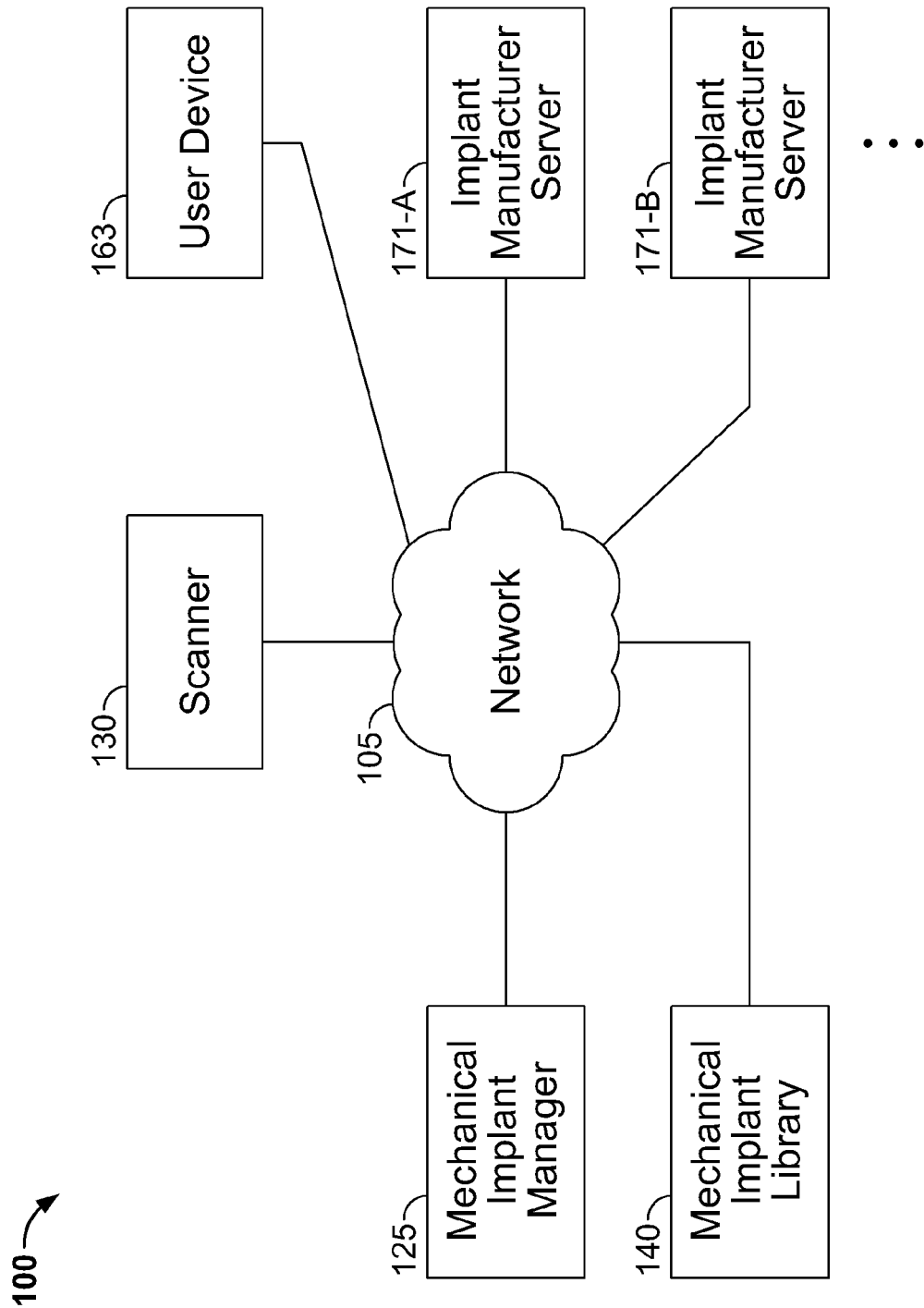
FIG. 1 shows a communication system in accordance with an embodiment.

FIG. 1 shows a communication system 100 in accordance with an embodiment. Communication system 100 includes a network 105, a mechanical implant manager 125, a mechanical implant library 140, a scanner 130, and a user device 163. In the embodiment of FIG. 1, a plurality of implant manufacturer servers, including implant manufacturer server 171-A and implant manufacturer server 171-B, are linked to network 105.

While two implant manufacturer servers 171 are shown in FIG. 1, in other embodiments communication system 100 may include more or fewer than two implant manufacturer servers.

Network 105 may comprise one or more of a number of different types of networks, such as, for example, an Internet, an intranet, a Fibre Channel-based storage area network (SAN), an iSCSI-based network, a local area network (LAN), a wide area network (WAN), or a wireless network. Other networks may be used. In other embodiments, network 105 may comprise a combination of two different types of networks.

Mechanical implant library 140 stores product information for a plurality of mechanical implants. For example, in one embodiment, mechanical implant library 140 may store, for each of a plurality of mechanical implants, recall information indicating whether a recall of the respective implant has been issued. In another example, mechanical implant library 140 may store, for each of a plurality of mechanical implants, expiration information indicating whether an expiration date of the respective implant has passed. In another embodiment, mechanical implant library 140 may store information specifying one or more medical procedures and, for each respective procedure, one or more mechanical implants that may be used in the procedure. Mechanical implant library 140 may also store one or more sets of rules that may be used to determine suitability of various mechanical implants for a specified medical procedure.

Mechanical implant library 140 may include one or more databases, tables, spreadsheets, files, etc., which store information. In the illustrative embodiment, mechanical implant library 140 comprises a mechanical implant database 142, shown in FIG. 2A, a medical procedure table 143, shown in FIG. 2B, and a plurality of rule sets, illustrated by FIGS. 2C and 2D. Mechanical implant library 140 may be implemented as a storage device, for example. Alternatively, mechanical implant library 140 may be implemented as a computer.

FIG. 2A shows mechanical implant database 142 in accordance with an embodiment. Database 142 stores product use information relating to various mechanical implants.

Database 142 comprises nine columns 281, 282, 283, 284, 285, 286, 287, 288, and 289. Column 281 stores an identifier of a respective mechanical implant. For example, a bar code, information associated with a bar code, or other type of identifier, may be stored in column 281. Column 282 stores a name of the respective mechanical implant. Column 283 indicates an implant type. For example, type information may be specified by a manufacturer, defined in accordance with industry standards, or may be defined in another manner. Column 284 specifies a lot number associated with the respective mechanical implant. The lot number may be, for example, an identifier of a lot or batch of mechanical implants produced at a particular facility. Column 285 specifies an implant system of the respective mechanical implant. For example, a system produced by a manufacturer may comprise one or more mechanical implants designed to function together. Column 286 contains a name of the manufacturer of the respective implant.

Columns 287, 288, and 289 store product use-related information for the mechanical implant identified in column 281. Specifically, column 287 stores expiration date information indicating an expiration date associated with the mechanical implant. Column 288 includes recall information indicating whether a recall of the mechanical implant has been issued. For example, column 285 may contain a date indicating when a recall was issued. Column 289 stores a location of a rule set associated with the respective mechanical implant. A rule set may be used to determine compatibility with other mechanical implants, for example. The location may include an address, a pointer to a record containing a set of rules, a name of a file containing a set of rules, a uniform resource locator, etc.

In the illustrative embodiment of FIG. 2A, records 291 and 292 contain information pertaining to two mechanical implants manufactured by a particular company named Company-1 and which function together in a system. Referring to record 291, a first mechanical implant is identified by identifier ID-1 (as indicated in column 281). Referring to columns 282 and 283, the name of the mechanical implant is "Knee A," and it is of a type referred to as "Type 1." Column 284 indicates that this mechanical implant was produced as part of lot number 1000. Columns 285 and 286 indicate that the mechanical implant is part of a system referred to as "System 2" manufactured by Company-1. The mechanical implant has an expiration date of Jan. 15, 2023, as indicated in column 287. Referring to column 288, a recall of the mechanical implant was issued on MM/DD/YYYY. Column 289 holds a location (such as an address) of a rule set (Rule Set 1) associated with this particular mechanical implant.

Record 292 stores information related to a particular mechanical implant identified by identifier ID-2 (as indicated in column 281). Referring to columns 282 and 283, the name of the mechanical implant is "Knee B," and it is of a type referred to as "Type 2." Column 284 indicates that this mechanical implant was produced as part of lot number 52300. Columns 285 and 286 indicate that the mechanical implant is part of the system referred to as "System 2" manufactured by Company-1. The mechanical implant has an expiration date of Jan. 15, 2023, as indicated in column 287. Referring to column 288, a recall of the mechanical implant was issued on MM/DD/YYYY. Column 289 holds a location of a rule set (Rule Set 2) associated with this particular mechanical implant.

Records 293 and 294 store information pertaining to two mechanical implants manufactured by a second company named Company-2. In particular, record 293 stores information related to a mechanical implant identified by identifier ID-3 (as indicated in column 281). Referring to columns 282 and 283, the name of the particular mechanical implant is "Artificial Knee P-1," and it is of the type referred to as "Type 1." Column 284 indicates that this mechanical implant was produced as part of lot number 16040. Columns 285 and 286 indicate that the mechanical implant is part of a system referred to as "System 3" manufactured by Company-2. The mechanical implant has no expiration date, as indicated in column 287. Referring to column 288, no recall of the mechanical implant has been issued. Column 289 holds a location of a rule set (Rule Set 3) associated with this particular mechanical implant.

Record 294 stores information related to a mechanical implant identified by identifier ID-4 (as indicated in column 281). Referring to columns 282 and 283, the name of the particular mechanical implant is "Artificial Knee P-2," and it is of the type referred to as "Type 2." Column 284 indicates that this mechanical implant was produced as part of lot number 3300. Columns 285 and 286 indicate that the mechanical implant is part of the system referred to as "System 3" manufactured by Company-2. The mechanical implant has no expiration date, as indicated in column 287. Referring to column 288, no recall of the mechanical implant has been issued. Column 289 holds a location of a rule set (Rule Set 4) associated with this particular mechanical implant.

Record 295 stores information related to a mechanical implant identified by identifier ID-5 (as indicated in column 281). Referring to columns 282 and 283, the name of the particular mechanical implant is "Knee Insert P-6," and it is of the type referred to as "Type 2." Column 284 indicates that this mechanical implant was produced as part of lot number 267. Columns 285 and 286 indicate that the mechanical implant is part of the system referred to as "System 4" manufactured by Company-2. The mechanical implant has no expiration date, as indicated in column 287. Referring to column 288, no recall of the mechanical implant has been issued. Column 289 holds a location of a rule set (Rule Set 5) associated with this particular mechanical implant.

In other embodiments, database 142 may have more or fewer than nine columns, and more or fewer than four records, and may store other types of information not shown in FIG. 2A.

FIG. 2B shows medical procedure table 143 in accordance with an embodiment. Medical procedure table 143 stores additional product use information that may be accessed by mechanical implant manager 125.

Medical procedure table 143 includes columns 261 and 262. Column 261 holds information identifying various medical procedures. Column 262 stores information indicating one or more types of mechanical implants that are associated with a specified medical procedure. Thus, record 271 identifies a procedure referred to as Procedure A, and specifies, in column 262, that when Procedure A is performed, mechanical implants of Type 1 and Type 2 may be used in the procedure. Record 272 identifies a procedure referred to as Procedure B, and specifies, in column 262, that when Procedure B is performed, mechanical implants of Type 3, Type 4, and Type 5 may to be used in the procedure.

FIG. 2C shows a rule set in accordance with an embodiment. Rule set 273, identified as "Rule Set 3," contains one or more rules. In the illustrative embodiment, a first rule 275 stored in rule set 273 indicates compatibility with another mechanical implant associated with the identifier ID-4. A second rule 276 comprises a body location requirement specifying the location on a patient's body where a mechanical implant must be used. In the illustrative embodiment, rule 276 requires use on the left side of the body.

FIG. 2D shows a rule set in accordance with an embodiment. Rule set 296, identified as "Rule Set 4," contains one or more rules. In the illustrative embodiment, a first rule 298 stored in rule set 296 indicates compatibility with another mechanical implant associated with the identifier ID-3. A second rule 299 stored in rule set 296 comprises a body location rule requiring use on the left side of the body.

In one embodiment, a stored rule set, such as Rule Set 273 and/or rule set 296, may include one or more selected rules without any information specifying a mechanical implant to which the rules are to be applied. The applicability of a particular rule set to a particular mechanical implant may be specified in the relevant record of database 142, for example, or elsewhere in mechanical implant library 140. In this manner, a particular rule set may be used in multiple instances, in relation to different mechanical implants, to determine suitability for a plurality of mechanical implants.

FIGS. 2C-2D are not to be construed as limiting. In other embodiments, a rule set may include other types of rules relating to other aspects of a mechanical implant, a medical procedure, a patient, etc., for use in determining suitability of a mechanical implant for a specified medical procedure.

Mechanical implant library 140 may also store other information not shown in FIGS. 2A-2D. For example, mechanical implant library 140 may store images of various mechanical implants, information indicating sizes of various mechanical implants, materials contained in various mechanical implants, fixation methods pertinent to various mechanical implants, etc.

In one embodiment, mechanical implant library 140 stores real-time, or near real-time, information received from one or more manufacturers, vendors, etc. For example, a manufacturer of a particular mechanical implant may transmit to mechanical implant manager 125 periodic updates relating to one or more mechanical implants produced by the manufacturer, including information concerning new products, recall information, expiration date information, compatibility information, etc. For example, mechanical implant manufacturer servers 171-A, 171-B, shown in FIG. 1, may be maintained by respective manufacturers of mechanical implants and provide real-time product-related information to mechanical implant manager 125. Mechanical implant manager 125 receives the information from the manufacturers and stores the information in mechanical implant library 140.

In the illustrative embodiment, mechanical implant manager 125 maintains mechanical implant library 140. In other embodiments, mechanical implant library 140 may be maintained by an entity different from mechanical implant manager 125. For example, one or more manufacturers of mechanical implants may maintain mechanical implant library 140. Alternatively, a hospital or other medical organization may maintain mechanical implant library 140. In another embodiment, a private entity may maintain mechanical implant library 140 and provide access to the mechanical implant library 140 as a service.

The embodiment shown in FIG. 1 is not to be construed as limiting. For example, while a single mechanical implant library 140 linked to network 105 and maintained by mechanical implant manager 125 is shown in the embodiment of FIG. 1, other arrangements are possible. For example, in one embodiment, mechanical implant library 140 may be stored locally, in memory 333 of mechanical implant manager 125. In another embodiment, one or more mechanical implant libraries may be maintained by a server associated with a manufacturer, such as server 171-A or 171-B. In some embodiments, multiple mechanical implant libraries may be maintained at various servers and maintained by respective manufacturers. Mechanical implant manager 125 may access the manufacturers' servers, and access the mechanical implant libraries to obtain information.

Scanner 130 may be any scanning device 130 capable of detecting identification information associated with a particular mechanical implant product. For example, in an illustrative embodiment, scanner 130 is a bar code scanning device. In this embodiment, scanner 130 is used from time to time to scan a bar code on a mechanical implant, or on a box holding a mechanical implant. Scanner 130 detects the bar code information and transmits the bar code information to mechanical implant manager 125.

While in the embodiment of FIG. 1, information identifying various mechanical implants is obtained by scanner 130, other systems, methods and apparatus may be used to obtain information identifying a mechanical implant. For example, in another embodiment, an image detection system may be used to obtain an image of a mechanical implant (or box containing a mechanical implant), and image analysis techniques may be used to identify the implant. In another embodiment, a user may read a code printed on the mechanical implant and enter the code into user device 163 or another device. In another embodiment, scanner 130 may comprise a radio frequency identification (RFID) device capable of detecting a signal produced by a RFID tag attached to a mechanical implant (or attached to a box holding an implant). Scanner 130 may extract selected information from the RFID signal and transmit the information to mechanical implant manager 125. Other methods and systems may be used to identify a mechanical implant.

User device 163 may be any device that enables a user to communicate via network 105. User device 163 may be connected to network 105 through a direct (wired) link, or wirelessly. User device 163 may have a display screen (not shown) for displaying information. For example, user device 163 may be a personal computer, a laptop computer, a workstation, a mainframe computer, a tablet computer, etc. Alternatively, user device 163 may be a mobile communication device such as a wireless phone, a personal digital assistant, etc. Other devices may be used.

In one embodiment, user device 163 and scanner 130 are combined in a single device. For example, user device 163 may be a computer having a bar code scanning functionality and an appropriate peripheral device capable of scanning a bar code.

User device 163 may display a graphical user interface that allows a user to interact with mechanical implant manager 125, scanner 130, mechanical implant library 140, etc. For example, user device 163 may display a graphical user interface that allows a user to specify or select a particular mechanical implant and to request information relating to the implant. User device 163 may, in response, transmit to mechanical implant manager 125 a request for information relating to the specified mechanical implant. Mechanical implant manager 125 may retrieve information from mechanical implant library 140 based on the request, and cause user device 163 to display the retrieved information on the graphical user interface.

Accordingly, mechanical implant manager 125 from time to time receives from user device 163 information identifying a mechanical implant. Mechanical implant manager 125 may also receive from user device 163 a request to determine the suitability of the mechanical implant for a particular medical procedure. In response, mechanical implant manager 125 retrieves product use information relating to the mechanical implant from mechanical implant library 140 and determines whether the mechanical implant is suitable for the medical procedure.

Figures 3, 4:
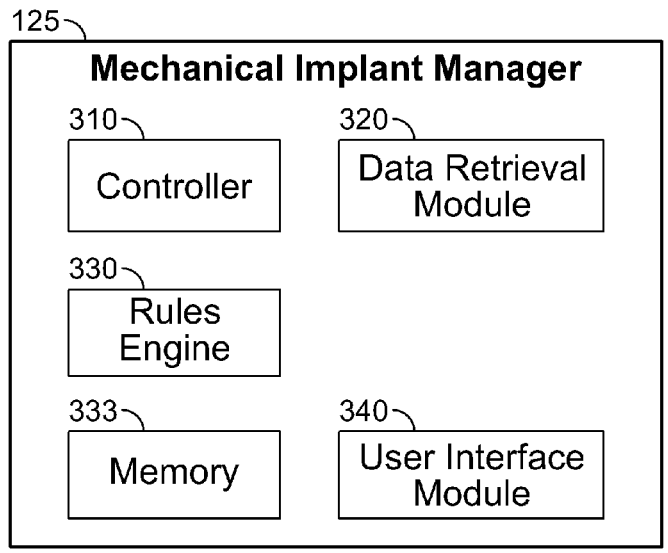
FIG. 3 shows components of a mechanical implant manager in accordance with an embodiment.
FIG. 4 shows a graphical user interface that may be provided by a mechanical implant manager in accordance with an embodiment.

FIG. 3 shows components of mechanical implant manager 125 in accordance with an embodiment. Mechanical implant manager 125 comprises a controller 310, a data retrieval module 320, a rules engine 330, a memory 333, and a user interface module 340. Controller 310 orchestrates the operation of various components of mechanical implant manager 125. For example, controller 310 may from time to time receive, from scanner 120, information (e.g., a bar code) identifying a particular mechanical implant and instruct data retrieval module 320 to obtain information relating to the identified mechanical implant. In response, data retrieval module 320 retrieves from mechanical implant library 140 information relating to a particular mechanical implant.

Memory 333 stores data. For example, memory 333 may from time to time be used by various components of mechanical implant manager 125 to store data generated during regular operation. Memory 333 may store any type of data such as files, databases, tables, etc.

Rules engine 330 applies one or more rules to determine the suitability of one or more selected mechanical implants for a particular medical procedure. Rules engine 330 may access a set of rules stored in mechanical implant library 140 and apply the rules to determine suitability of one or more mechanical implants. For example, rules engine 330 may access Rule Set 3 (273) shown in FIG. 2C and/or Rule Set 4 (296) shown in FIG. 2D, and use the rules therein to determine suitability of one or more mechanical implants.

Rules engine 330 may also include one or more rules of general application. For example, rules engine 330 may include a rule that stipulates that any mechanical implant for which a recall has been issued is not suitable for use. Rules engine 330 may also include a rule that stipulates that a mechanical implant is not suitable for use if the relevant expiration date has passed.

User interface module 340 from time to time communicates with user device 163 to facilitate use of mechanical implant manager 125 by doctors and/or other practitioners. For example, user interface module 340 may cause user device 163 to display a graphical user interface to enable a practitioner to view information concerning a particular mechanical implant, or to enable the practitioner to provide information.

In one embodiment, mechanical implant library 140 and mechanical implant manager 125 reside on one or more server computers maintained at a hospital or other medical facility. Scanner 130 is a bar code scanning device located in or near an operating room in the hospital. User device 163 is a personal computer or other processing device also located in or near the operating room. Network 105 may be the Internet or a local area network maintained by the hospital.

In accordance with an embodiment, a user (such as a doctor or other practitioner) who is performing a medical procedure, may utilize mechanical implant manager 125 to verify the suitability of a particular mechanical implant for the procedure.

In the illustrative embodiment, a practitioner, such as a doctor, is in an operating room of a hospital or other surgical facility, performing a medical procedure to implant an artificial knee into a patient's leg. During the procedure, the practitioner employs user device 163 to access mechanical implant manager 125 and verify the suitability of one or more mechanical implants for the medical procedure.

In order to access mechanical implant manager 125, the practitioner may log into mechanical implant manager 125, for example. When the practitioner accesses mechanical implant manager 125, user interface module 340 may cause user device 163 to display a graphical user interface such as that shown in FIG. 4. Graphical user interface 400 includes a name field 410, in which the practitioner may enter his or her name, and a password field 420, in which the practitioner may enter a password. Graphical user interface 400 also includes a field 430 in which the practitioner may specify the medical procedure which is to be performed, a primary implant system field 431, in which the practitioner may specify a preferred implant system, and a location of implant field 432, in which the practitioner may indicate, for example, a side of the patient's body the procedure will be performed on. In other embodiments, other type of body location information may be entered, such as "heart," "colon," etc. In the illustrative embodiment, the practitioner enters "Procedure A" in field 430, "System 2" in field 431 and "Left" in field 432. User interface module 340 receives the medical procedure information, the primary system information, and the body location information entered by the practitioner and forwards the information to controller 310.

Figure 5:
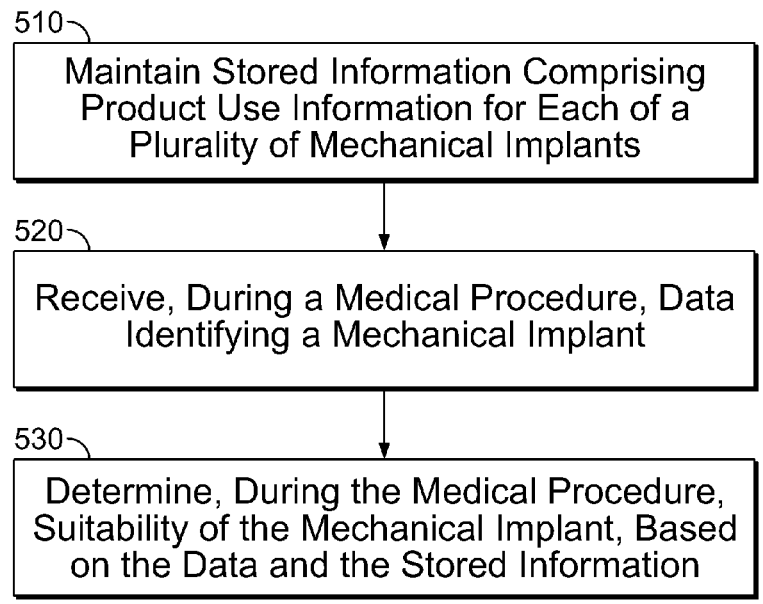
FIG. 5 is a flowchart of a method of verifying a suitability of a mechanical implant for a medical procedure in accordance with an embodiment.

After logging in and specifying the information listed on graphical user interface 400, the practitioner may use mechanical implant manager 125 to determine the suitability of one or more mechanical implants for the medical procedure. FIG. 5 is a flowchart of a method of verifying a suitability of a mechanical implant for a medical procedure in accordance with an embodiment. At step 510, stored information comprising product use information for each of a plurality of mechanical implants is maintained. As discussed above, mechanical implant library 140, comprising product use information pertaining to various mechanical implants, is maintained by mechanical implant manager 125.

In one embodiment, the information specifying the medical procedure to be performed (entered by the practitioner in field 430 of graphical user interface 400) is used to select one or more graphical user interfaces that are subsequently displayed. In the illustrative embodiment, data retrieval module 320 (of mechanical implant manager 125) receives the medical procedure information (specifying "Procedure A") entered by the practitioner, and accesses mechanical implant library 140 to obtain additional information concerning the medical procedure to be performed. In the illustrative embodiment, data retrieval module 320 accesses medical procedure table 143 and determines that record 271 is associated with Procedure A. Data retrieval module 320 determines that a Type 1 implant and a Type 2 implant are associated with Procedure A.

Figure 6A:
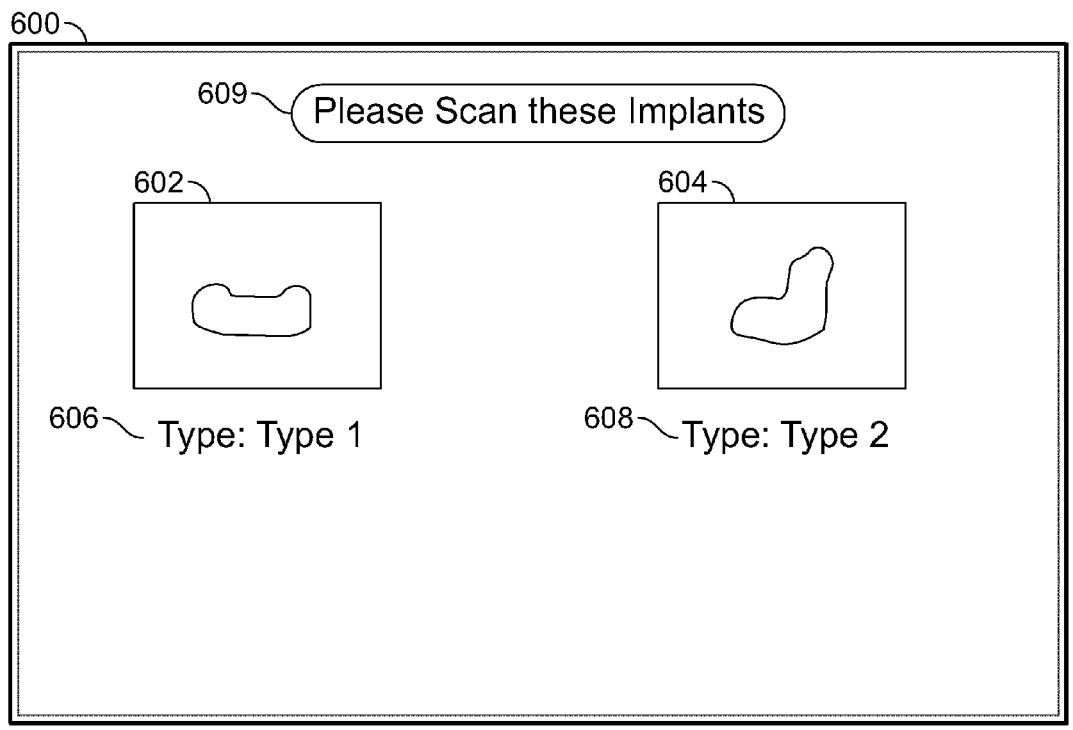
FIGS. 6A-6F show graphical user interfaces that may be provided by a mechanical implant manager in accordance with an embodiment.

Accordingly, user interface module 340 causes user device 163 to display a graphical user interface such as that shown in FIG. 6A. Graphical user interface 600 shows a first image 602 of a mechanical implant of Type 1, a type indicator 606 indicating that the mechanical implant is a Type 1 implant, and a second image 604 of a second mechanical implant of Type 2, and a second type indicator 608 indicating that the second mechanical implant is a Type 2 implant. Graphical user interface 600 also includes an instruction (609) "Please Scan the Implants."

The practitioner knows of several different mechanical implants that are available and may serve the required purpose, and selects a particular pair of mechanical implants manufactured by a company named Company-1. For example, the practitioner may prefer the mechanical implants of Company-1 because the practitioner used them previously and was satisfied with the results. The practitioner instructs an assistant to retrieve the selected mechanical implants from the appropriate inventory in the hospital. The assistant leaves the operating room and returns with two boxes containing the selected mechanical implants.

At step 520, data identifying a mechanical implant is received during a medical procedure. The practitioner obtains one of the two boxes retrieved by the assistant, and uses scanner 130 to scan the bar code on the box. Scanner 130 transmits the bar code, or data representing the bar code, to mechanical implant manager 125. User interface module 340 receives the bar code data and forwards the bar code data to controller 310. Controller 310 determines an identifier associated with the bar code information. In the illustrative embodiment, controller 310 analyzes the bar code information and determines that the identifier associated with the bar code is ID-1.

Controller 310 provides the identifier (ID-1) to data retrieval module 320 and instructs data retrieval module 320 to retrieve product use information for the mechanical implant identified by the identifier ID-1. In response, data retrieval module 320 accesses database 142 of mechanical implant library 140, and identifies records associated with the identifier ID-1. Referring to FIG. 2A, data retrieval module 320 determines that record 291 contains identifier ID-1. Data retrieval module 320 accordingly accesses record 291 and retrieves the information stored in columns 282-289. Specifically, data retrieval module 320 retrieves implant name and type information stored in columns 282 and 283, lot number information stored in column 284, implant system information stored in column 285, manufacturer information stored in column 286, expiration date information and recall information stored in columns 287 and 288, and the rules set location information stored in column 289.

In the illustrative embodiment, data retrieval module 320 also retrieves from mechanical implant library 140 an image of the mechanical implant associated with the identifier ID-1.

At step 530, suitability of the mechanical implant is determined, during the medical procedure, based on the data and the stored information. In the illustrative embodiment, rules engine 330 examines the recall information retrieved from column 288 of record 291, indicating that a recall of the mechanical implant was issued on date MM/DD/YYYY, and determines that the mechanical implant identified by identifier ID-1 is not suitable for use.

Figure 6B:
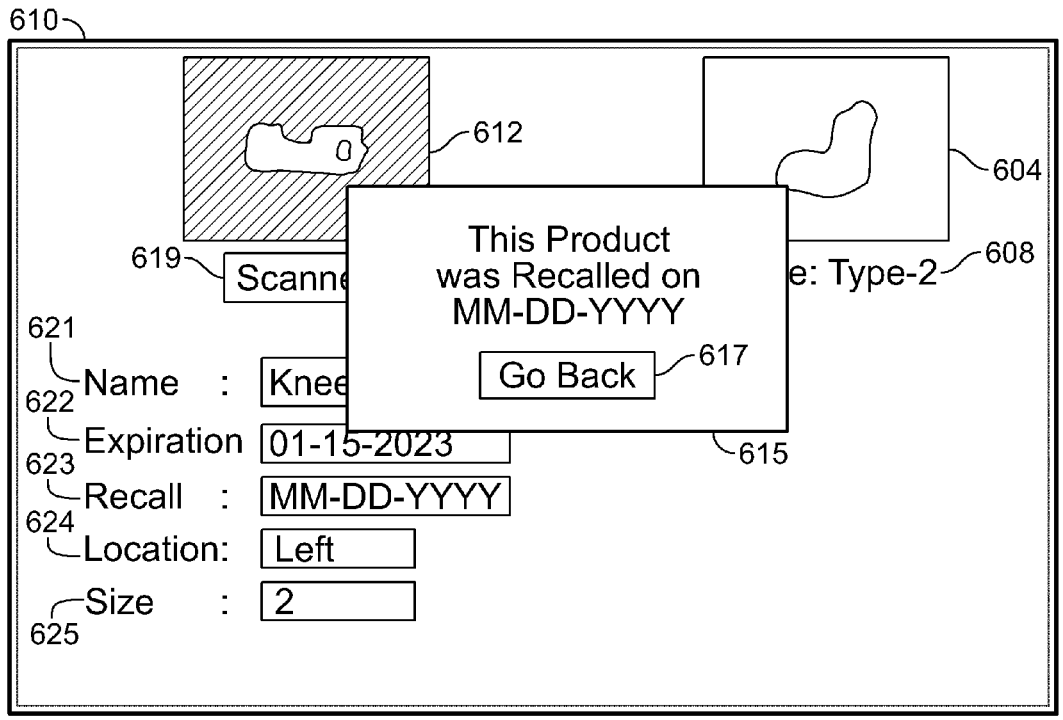

User interface module 340 accordingly causes user device 163 to display a graphical user interface such as that shown in FIG. 6B. Graphical user interface 610 shows an image 612 of the mechanical implant identified by the identifier ID-1 and an icon 619 stating that the implant has been "SCANNED." Graphical user interface 610 also includes a name field 621, an expiration date field 622, a recall information field 623, a location field 624, and a size field 625, in which selected items of information retrieved from mechanical implant library 140 are displayed.

In the illustrative embodiment, graphical user interface 610 also displays a notice 615 stating "This Product Was Recalled on MM-DD-YYYY".

In the illustrative embodiment, the practitioner views the recall message and, in response, decides not to use the selected mechanical implants. Instead, the practitioner selects, as an alternative, a different pair of mechanical implants for use in the medical procedure. In the illustrative embodiment, the practitioner selects the mechanical implants identified by the identifiers ID-3 and ID-5 (shown in FIG. 2A), believing that these two mechanical implants are compatible and suitable for the desired medical procedure. The practitioner asks the assistant to retrieve the alternative mechanical implants.

Because the practitioner now wishes to scan a different pair of mechanical implants, the practitioner may restart the process described above with reference to FIGS. 6A-6B. In the illustrative embodiment, the practitioner may press a "Go Back" button 617 displayed on graphical user interface 610 to return to graphical user interface 600. Other methods may be used to navigate among various graphical user interfaces provided by mechanical implant manager 125.

The assistant leaves the operating room and returns with two boxes containing the alternative mechanical implants. The practitioner selects one of the boxes retrieved by the assistant, and uses scanner 130 to scan the bar code on the box. Scanner 130 transmits the bar code, or data representing the bar code, to mechanical implant manager 125. User interface module 340 receives the bar code data and forwards the bar code data to controller 310. Controller 310 analyzes the bar code and determines that the identifier associated with the bar code is ID-3. Data retrieval module 320 accesses database 142 and retrieves information pertaining to the mechanical implant identified by the identifier ID-3. Specifically, data retrieval module 320 retrieves product use information from record 293. In the illustrative embodiment, data retrieval module 320 also retrieves from mechanical implant library 140 an image of the mechanical implant associated with the identifier ID-3.

Rules engine 330 determines that the mechanical implant associated with record 293 has no expiration date and that no recall has been issued.

Figure 6C:
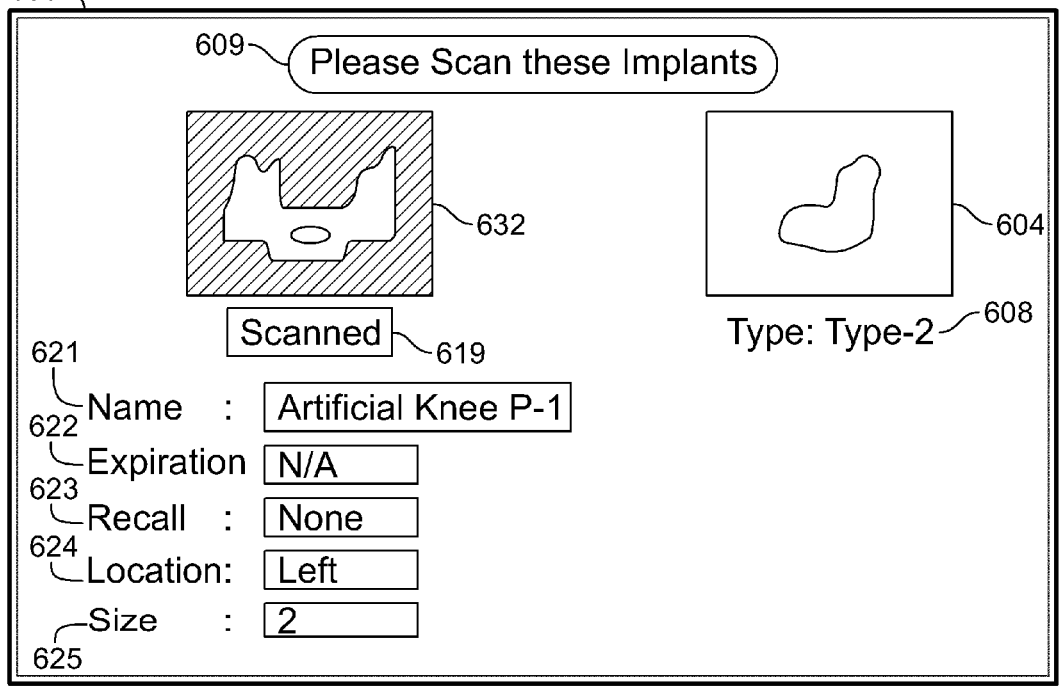

User interface module 340 causes user device 163 to display a graphical user interface such as that shown in FIG. 6C. Graphical user interface 630 shows an image 632 of the mechanical implant identified by the identifier ID-3 and an icon 619 stating that the implant has been "SCANNED." Graphical user interface 630 also includes name field 621, expiration date field 622, recall information field 623, location field 624, and size field 625, in which selected items of information retrieved from mechanical implant library 140 are displayed.

The practitioner may review the information displayed on graphical user interface 670 to confirm that the mechanical implant is in fact the device that he or she selected.

Figure 6D:
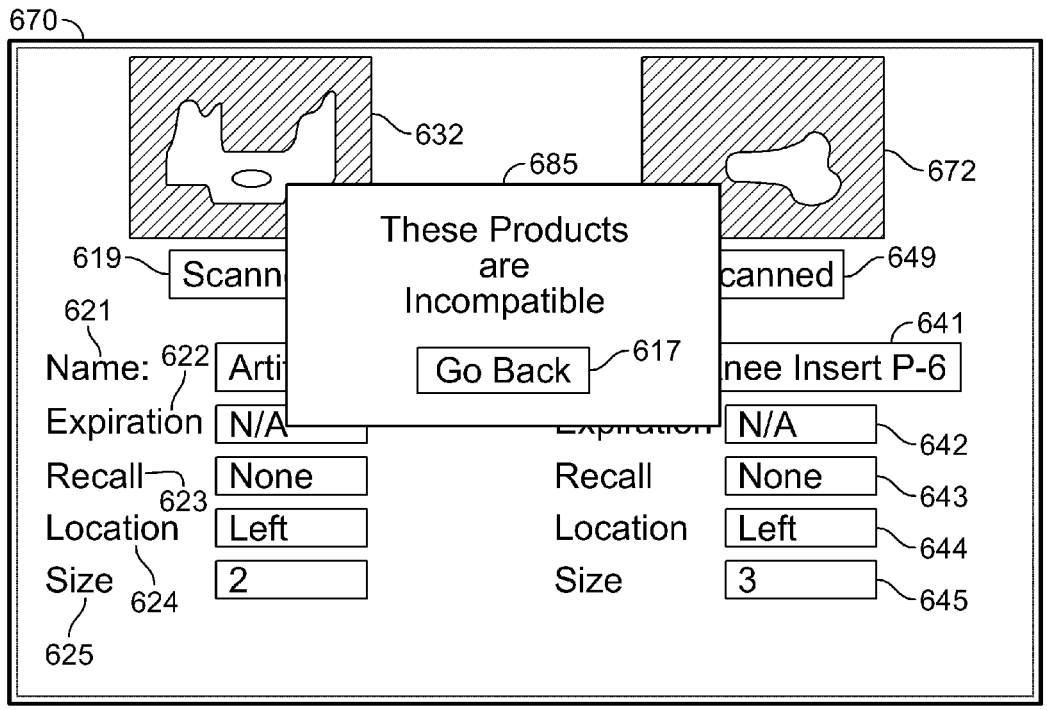

In the illustrative embodiment, the practitioner then uses scanner 130 to scan the second box and, in a similar manner obtains a graphical user interface showing information relating to the mechanical implant associated with identifier ID-5, as shown in FIG. 6D. Graphical user interface 670 displays the information already obtained which relates to the mechanical implant identified by the identifier ID-3, and additionally shows information for the newly scanned mechanical implant. Specifically, graphical user interface 640 displays an image 672 of the mechanical implant identified by the identifier ID-5 and an icon 649 stating that the implant has been "SCANNED." Graphical user interface 670 also includes a name field 641, an expiration date field 642, a recall information field 643, a location field 644, and a size field 645, in which selected items of information retrieved from mechanical implant library 140 are displayed.

Rules engine 330 now accesses one or more rule sets applicable to the two mechanical implants that have been scanned. In the illustrative embodiment, rules engine 330 accesses record 293 of database 142 and retrieves the rule set location information stored in column 289. Specifically, rules engine 330 retrieves the information indicating the location of Rule Set 3, and uses the information to access Rule Set 3. Referring to FIG. 2C, rules engine 330 applies one or more rules stored in Rules Set 3 (273) to determine suitability of the mechanical implant identified by identifier ID-3 for the present medical procedure. In the illustrative embodiment, rules engine 330 examines rule 275, which stipulates that the relevant mechanical implant is compatible with the mechanical implant identified by identifier ID-4. Since rule 275 does not indicate compatibility with the mechanical implant identified by the identifier ID-5 (and no other rule in Rule Set (275) does so), rules engine 330 concludes that the mechanical implant identified by the identifier ID-3 is incompatible with the mechanical implant identified by the identifier ID-5. Rules engine 330 accordingly informs controller 310 that the two mechanical implants are incompatible.

Referring again to FIG. 6D, user interface module 340 now causes user device 163 to display a message 685 stating, "These Products are Incompatible".

The practitioner views message 685 and, in response, decides to use instead the mechanical implants identified by the identifiers ID-3 and ID-4. The practitioner asks the assistant to retrieve the mechanical implant identified by the identifier ID-4. The assistant leaves the room and returns with a box containing the mechanical implant identified by identifier ID-4.

The practitioner may again restart the process described above with reference to FIGS. 6A-6B by pressing "Go Back" button 617 displayed on graphical user interface 670 to return to graphical user interface 600.

Figure 6E:
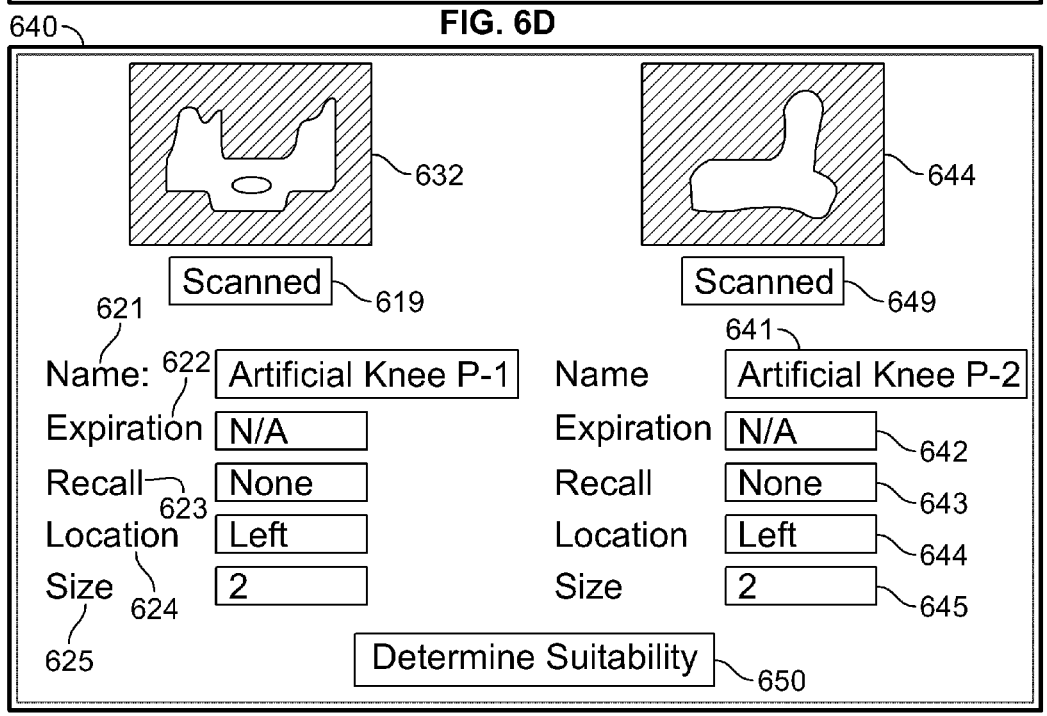

In the illustrative embodiment, the practitioner uses scanner 130 to rescan the box containing the mechanical implant identified by the identifier ID-3, and then scans the box containing the mechanical implant identified by the identifier ID-4, and obtains a graphical user interface showing information relating to the two scanned mechanical implants. Referring to FIG. 6E, graphical user interface 640 displays the information relating to the mechanical implant identified by the identifier ID-3, and additionally shows information for the mechanical implant identified by identifier ID-4. Specifically, graphical user interface 640 displays information relating to the mechanical implant identified by identifier ID-3, as described above, and also displays an image 644 of the mechanical implant identified by the identifier ID-4, and an icon 649 stating that the implant has been "SCANNED." Graphical user interface 640 also includes name field 641, expiration date field 642, recall information field 643, location field 644, and size field 645, in which selected items of information retrieved from mechanical implant library 140 are displayed.

After the practitioner confirms that the mechanical implants displayed on graphical user interface 640 are the implants that he or she had selected, the practitioner may select a Determine Suitability option 650. In response, user device 163 transmits to mechanical implant manager 125 a request to verify the suitability of the mechanical implants associated with identifier ID-3 and ID-4 for the specified medical procedure. The request may include the identifiers ID-3 and ID-4 and information identifying the medical procedure, for example. Controller 310 (of mechanical implant manager 125) receives the request.

Controller 310 invokes rules engine 330 to determine the suitability of the mechanical implants for the specified medical procedure. Accordingly, rules engine 330 accesses records 293 and 294 in database 142, and examines the product information stored therein. Rules engine 330 determines that the two mechanical implants identified by identifiers ID-3 and ID-4 have no expiration date, and that no recall has been issued for these two implants.

Rules engine 330 now accesses the rule set address information stored in records 293 and 294 to determine any applicable rules. In the illustrative embodiment, rules engine 330 uses the rule set location information in column 289 of record 293 to access Rule Set 3 (273), shown in FIG. 2C. Rule Set 3 (273) contains a set of rules applicable to the mechanical implant identified by the identifier ID-3, and includes rule 275 indicating that the mechanical implant is compatible with the mechanical implant identified by the identifier ID-4. Rules engine 330 applies the compatibility rule 275 specified in Rule Set 3 (273) and determines that the mechanical implant identified by the identifier ID-3 (scanned by the practitioner) is compatible with the mechanical implant identified by the identifier ID-4.

Rules engine 330 also examines rule 276, which requires that the mechanical implant be used on the left side of a patient's body. Rules engine 330 applies this rule to the body location information previously provided by the practitioner (in location field 432 of graphical user interface 400), and determines that the mechanical implant identified by identifier ID-3 is suitable for the present medical procedure.

Rules engine 330 performs a similar analysis to determine suitability of the mechanical implant identified by identifier ID-4 for the specified medical procedure. Rules engine 330 accesses record 294 in database 142, and examines the rule set address information in the record. In the illustrative embodiment, rules engine 330 uses the rule set location information in column 289 of record 294 to access Rule Set 4 (296), shown in FIG. 2D. Rule Set 4 (296) contains a set of rules applicable to the mechanical implant identified by the identifier ID-4, and includes a rule 298 indicating that the mechanical implant is compatible with the mechanical implant identified by the identifier ID-3. Rules engine 330 applies the compatibility rule 298 specified in Rule Set 4 (296) and determines that the mechanical implant identified by the identifier ID-4 (scanned by the practitioner) is compatible with the mechanical implant identified by the identifier ID-3.

Rules engine 330 also examines rule 299, which requires that the mechanical implant be used on the left side of a patient's body. Rules engine 330 applies this rule to the body location information previously provided by the practitioner (in location field 432 of graphical user interface 400), and determines that the mechanical implant identified by identifier ID-4 is suitable for the present medical procedure.

In other embodiments, rules engine 330 may examine and apply any number of rules, including other types of rules relating to other aspects of a mechanical implant, a medical procedure, a patient, etc., to determine suitability of a mechanical implant for a specified medical procedure.

In this manner, rules engine 330 therefore determines that the mechanical implants identified by the identifiers ID-3 and ID-4 are compatible, and are suitable for the procedure to be performed.

Figure 6F:
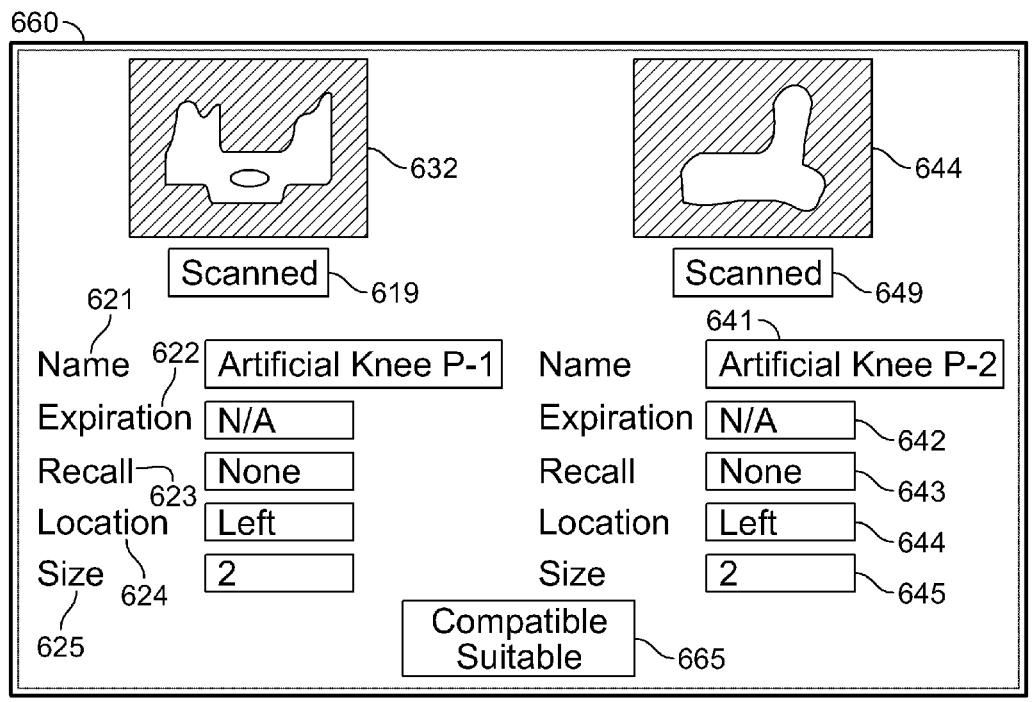

User interface module 340 now causes user device 163 to display a graphical user interface such as that shown in FIG. 6F. Graphical user interface 660 includes the information displayed on graphical user interface 640 (of FIG. 6E) and additionally displays a message 665 indicating that the mechanical implants are "Compatible" and "Suitable".

In the illustrative embodiment, the practitioner reviews the information on graphical user interface 660 and, satisfied that the two mechanical implants are compatible and suitable for the specified medical procedure, proceeds to perform the medical procedure.

In various embodiments, the method steps described herein, including the method steps described in FIG. 5, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
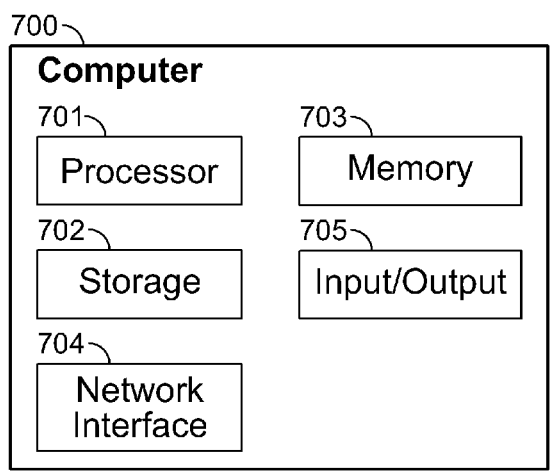
FIG. 7 shows components of an exemplary computer that may be used to implement certain embodiments of the invention.

A high-level block diagram of an exemplary computer that may be used to implement systems, apparatus and methods described herein is illustrated in FIG. 7. Computer 700 includes a processor 701 operatively coupled to a data storage device 702 and a memory 703. Processor 701 controls the overall operation of computer 700 by executing computer program instructions that define such operations. The computer program instructions may be stored in data storage device 702, or other computer readable medium, and loaded into memory 703 when execution of the computer program instructions is desired. Thus, the method steps of FIG. 5 can be defined by the computer program instructions stored in memory 703 and/or data storage device 702 and controlled by the processor 701 executing the computer program instructions. For example, the computer program instructions can be implemented as computer executable code programmed by one skilled in the art to perform an algorithm defined by the method steps of FIG. 5. Accordingly, by executing the computer program instructions, the processor 701 executes an algorithm defined by the method steps of FIG. 5. Computer 700 also includes one or more network interfaces 704 for communicating with other devices via a network. Computer 700 also includes one or more input/output devices 705 that enable user interaction with computer 700 (e.g., display, keyboard, mouse, speakers, buttons, etc.).

Processor 701 may include both general and special purpose microprocessors, and may be the sole processor or one of multiple processors of computer 700. Processor 701 may include one or more central processing units (CPUs), for example. Processor 701, data storage device 702, and/or memory 703 may include, be supplemented by, or incorporated in, one or more application-specific integrated circuits (ASICs) and/or one or more field programmable gate arrays (FPGAs).

Data storage device 702 and memory 703 each include a tangible non-transitory computer readable storage medium. Data storage device 702, and memory 703, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 705 may include peripherals, such as a printer, scanner, display screen, etc. For example, input/output devices 705 may include a display device such as a cathode ray tube (CRT) or liquid crystal display (LCD) monitor for displaying information to the user, a keyboard, and a pointing device such as a mouse or a trackball by which the user can provide input to computer 700.

Any or all of the systems and apparatus discussed herein, including mechanical implant manager 125, scanner 130, user device 163, implant manufacturer servers 171, and mechanical implant library 140, and components thereof, including controller 310, data retrieval module 320, rules engine 330, and user interface module 340, may be implemented using a computer such as computer 700.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of verifying compatibility of an implant for a specified medical procedure, the method comprising:
   maintaining stored information comprising product use information for each of a plurality of implants, the product use information specifying a respective body location associated with each of the plurality of implants;
   receiving, during the specified medical procedure, data identifying an implant;
   receiving second data identifying a body location associated with the specified medical procedure; and
   determining, during the medical procedure, compatibility of the implant, based on the data, the second data, and the stored information.

2. The method of claim 1, wherein receiving data identifying the implant further comprises:
   detecting a bar code associated with the implant;
   the method further comprising:
   identifying the implant based on the bar code and the stored information.

3. The method of claim 1, wherein the product use information comprises second information indicating whether the implant is compatible with a second implant, the method further comprising:
   receiving, during the medical procedure, third data identifying the second implant; and
   determining, during the medical procedure, whether the implant is compatible with the second implant, based on the data, the third data, and the second information.

4. The method of claim 3, wherein the second information comprises a stored rule.

5. The method of claim 1, wherein the product use information comprises recall information indicating whether a recall of the implant has been issued, the method further comprising:
   determining, during the medical procedure, that a recall of the implant has been issued, based on the data and the recall information.

6. The method of claim 1, wherein the product use information comprises expiration information indicating whether an expiration date of the implant has passed, the method further comprising:
   determining, during the medical procedure, that the expiration date of the implant has passed, based on the data and the expiration information.

7. The method of claim 1, further comprising:
accessing a stored rule associated with the implant, and
wherein determining compatibility of the implant further comprises:
determining compatibility of the implant based on the rule.

8. A computer readable medium having program instructions stored thereon, that, in response to execution by a processor, cause the processor to perform operations comprising:
maintaining stored information comprising product use information for each of a plurality of implants, the product use information specifying a respective body location associated with each of the plurality of implants;
receiving, during a specified medical procedure, data identifying an implant;
receiving second data identifying a body location associated with the specified medical procedure; and
determining, during the specified medical procedure, compatibility of the implant, based on the data, the second data, and the stored information.

9. The computer readable medium of claim 8, the operations further comprising:
detecting a bar code associated with the implant; and
identifying the implant based on the bar code and the stored information.

10. The computer readable medium of claim 8, wherein the product use information comprises second information indicating whether the implant is compatible with a second implant, the operations further comprising:
receiving, during the medical procedure, third data identifying the second implant; and
determining, during the medical procedure, whether the implant is compatible with the second implant, based on the data, the third data, and the second information.

11. The computer readable medium of claim 10, wherein the second information comprises a stored rule.

12. The computer readable medium of claim 8, wherein the product use information comprises recall information indicating whether a recall of the implant has been issued, the operations further comprising:
determining, during the medical procedure, that a recall of the implant has been issued, based on the data and the recall information.

13. The computer readable medium of claim 8, wherein the product use information comprises expiration information indicating whether an expiration date of the implant has passed, the operations further comprising:
determining, during the medical procedure, that the expiration date of the implant has passed, based on the data and the expiration information.

14. The computer readable medium of claim 8, the operations further comprising:
accessing a stored rule associated with the implant, and
wherein determining compatibility of the implant further comprises:
determining compatibility of the implant based on the rule.

15. A system comprising:
a first memory storing information comprising product use information for each of a plurality of implants, the product use information specifying a respective body location associated with each of the plurality of implants;
a scanner;
a second memory storing computer program instructions; and
a processor communicatively coupled to the second memory, the processor configured to execute the computer program instructions which, when executed on the processor, cause the processor to perform operations comprising:
receiving, during a specified medical procedure, from the scanner, data identifying an implant;
retrieving from the first memory selected information related to the implant;
receiving second data identifying a body location associated with the specified medical procedure; and
determining, during the specified medical procedure, suitability of the implant, based on the data, the second data, and the selected information.

16. The system of claim 15, wherein receiving data identifying the implant further comprises:
detecting a bar code associated with the implant; and
identifying the implant based on the bar code.

17. The system of claim 15, wherein the product use information comprises second information indicating whether the implant is compatible with a second implant, the operations further comprising:
receiving, during the medical procedure, third data identifying the second implant; and
determining, during the medical procedure, whether the implant is compatible with the second implant, based on the data, the third data, and the second information.

18. The system of claim 15, wherein the product use information comprises recall information indicating whether a recall of the implant has been issued, the operations further comprising:
determining, during the medical procedure, that a recall of the implant has been issued, based on the data and the recall information.

19. The system of claim 15, wherein the product use information comprises expiration information indicating whether an expiration date of the implant has passed, the operations further comprising:
determining, during the medical procedure, that the expiration date of the implant has passed, based on the data and the expiration information.

20. The system of claim 15, the operations further comprising:
accessing a stored rule associated with the implant, and
wherein determining compatibility of the implant further comprises:
determining compatibility of the implant based on the rule.

* * * * *

UNITED STATES PATENT AND TRADEMARK OFFICE
CERTIFICATE OF CORRECTION

PATENT NO. : 9,050,063 B2
APPLICATION NO. : 13/835494
DATED : June 9, 2015
INVENTOR(S) : Michael Roe et al.

It is certified that error appears in the above-identified patent and that said Letters Patent is hereby corrected as shown below:

In the Claims:

Claim 1, at column 16, line 34 the text "determining, during the medical procedure" should read --determining, during the specified medical procedure--

Claim 3, at column 16, line 47 the text "receiving, during the medical procedure" should read --receiving, during the specified medical procedure--

Claim 5, at column 16, line 58 the text "determining, during the medical procedure" should read --determining, during the specified medical procedure--

Claim 6, at column 16, line 65 the text "determining, during the medical procedure" should read --determining, during the specific medical procedure--

Claim 10, at column 17, line 30 the text "receiving, during the medical procedure" should read --receiving, during the specified medical procedure--

Claim 12, at column 17, line 41 the text "determining, during the medical procedure" should read --determining, during the specified medical procedure--

Claim 13, at column 17, line 48 the text "determining, during the medical procedure" should read --determining, during the specified medical procedure--

Claim 17, at column 18, line 30 the text "receiving, during the medical procedure" should read --receiving, during the specified medical procedure--

Claim 18, column 18, at line 39 the text "determining, during the medical procedure" should read --determining, during the specific medical procedure--

Claim 19, at column 18, line 46 the text "determining, during the medical procedure" should read --determining, during the specific medical procedure--

Signed and Sealed this
Ninth Day of August, 2016

Michelle K. Lee
*Director of the United States Patent and Trademark Office*